United States Patent
Hirai et al.

(10) Patent No.: US 10,759,768 B2
(45) Date of Patent: Sep. 1, 2020

(54) PROPHYLACTIC OR THERAPEUTIC AGENT FOR AUTISM SPECTRUM DISORDER

(71) Applicant: TAKEDA PHARMACEUTICAL COMPANY LIMITED, Osaka (JP)

(72) Inventors: Keisuke Hirai, Kanagawa (JP); Takashi Ishikawa, Kanagawa (JP)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 16/068,553

(22) PCT Filed: Jan. 5, 2017

(86) PCT No.: PCT/JP2017/000166
§ 371 (c)(1),
(2) Date: Jul. 6, 2018

(87) PCT Pub. No.: WO2017/119455
PCT Pub. Date: Jul. 13, 2017

(65) Prior Publication Data
US 2019/0040022 A1    Feb. 7, 2019

Related U.S. Application Data

(60) Provisional application No. 62/276,354, filed on Jan. 8, 2016.

(51) Int. Cl.
| | | |
|---|---|---|
| C07D 263/52 | (2006.01) | |
| C07D 413/06 | (2006.01) | |
| C07D 277/60 | (2006.01) | |
| A61P 25/00 | (2006.01) | |
| A61K 31/428 | (2006.01) | |
| A61K 31/423 | (2006.01) | |

(52) U.S. Cl.
CPC .......... *C07D 263/52* (2013.01); *A61K 31/423* (2013.01); *A61K 31/428* (2013.01); *A61P 25/00* (2018.01); *C07D 277/60* (2013.01); *C07D 413/06* (2013.01)

(58) Field of Classification Search
CPC .. C07D 263/52; C07D 413/06; C07D 277/60; A61P 25/00
USPC ....................................................... 514/338
See application file for complete search history.

(56) References Cited

U.S. PATENT DOCUMENTS

| | | | |
|---|---|---|---|
| 5,910,492 A | 6/1999 | Hoshino et al. | |
| 8,030,337 B2* | 10/2011 | Uchikawa | C07D 263/52 514/375 |
| 8,110,585 B2 | 2/2012 | Koike et al. | |
| 8,236,837 B2* | 8/2012 | Uchikawa | C07D 263/52 514/375 |
| 8,247,429 B2 | 8/2012 | Uchikawa et al. | |
| 8,273,761 B2 | 9/2012 | Uchikawa et al. | |
| 2010/0010038 A1 | 1/2010 | Uchikawa et al. | |
| 2010/0029707 A1 | 2/2010 | Uchikawa et al. | |
| 2010/0130538 A1 | 5/2010 | Koike et al. | |
| 2019/0008834 A1* | 1/2019 | Mahableshwarkar | A61K 31/423 |

FOREIGN PATENT DOCUMENTS

| | | |
|---|---|---|
| JP | H09-263545 A | 10/1997 |
| JP | 2009-541202 A | 11/2009 |
| WO | 1996/008466 A1 | 3/1996 |
| WO | 1997/001539 A1 | 1/1997 |
| WO | 1997/005098 A1 | 2/1997 |
| WO | 1997/032871 A1 | 9/1997 |
| WO | 2007/134077 A2 | 11/2007 |
| WO | 2007/148808 A1 | 12/2007 |
| WO | 2008/069311 A1 | 6/2008 |
| WO | 2008/084717 A1 | 7/2008 |
| WO | 2008/136382 A1 | 11/2008 |

OTHER PUBLICATIONS

"Autism Spectrum Disorder," Diagnostic and Statistical Manual of Psychiatric Disorders, 5th Edition, 2013, p. 50-59.
International Search Report and Written Opinion for Application No. PCT/JP2017/000166 dated Mar. 14, 2017 (7 pages).
Kumar et al., "Benefits of agomelatine in behavioral, neurochemical and blood brain barrier alterations in prenatal valproic acid induced autism spectrum disorder," Neurochemistry International, 2015, 91: 34-45.
Melke et. al., "Abnormal melatonin synthesis in autism spectrum disorders," Mol Psychiatry, 2008, 13(1):90-8.
Rossingnol et al., "Melatonin in autism spectrum disorders: a systematic review and meta-analysis," Developmental Medicine & Child Neurology, 2011, 53(9): 783-792.
Stigler et., "Ramelteon for Insomnia in Two Youths with Austitic Disorder," J Child Adolesc Psychopharmacol, 2006, 16(5):631-6.
Tordjman et al., "Advances in the Research of Melatonin in Autism Spectrum Disorders: Literature Review and New Perspectives," International Journal of Molecular Sciences, 2013, 14: 20508-20542.

(Continued)

*Primary Examiner* — Niloofar Rahmani
(74) *Attorney, Agent, or Firm* — Michael Best & Friedrich LLP

(57) ABSTRACT

The present invention provides a prophylactic or therapeutic agent for an autism spectrum disorder containing compound (I) having melatonin receptor affinity. A compound represented by the formula:

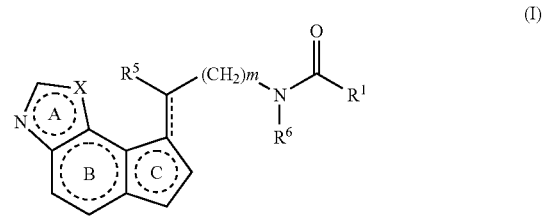

wherein each symbol is as described in the specification, or a salt thereof.

3 Claims, 1 Drawing Sheet

(56) References Cited

OTHER PUBLICATIONS

Tordjman et. al., "Day and nighttime excretion of 6-sulphatoxymelatonin in adolescents and young adults with autistic disorder," Psychoneuroendocrinology, 2012, 37(12):1990-7.

Wirojanan et. al., "The efficacy of melatonin for sleep problems in children with autism, fragile X syndrome, or autism and fragile X syndrome," J Clin Sleep Med, Apr. 2009, 5(2):145-50.

* cited by examiner

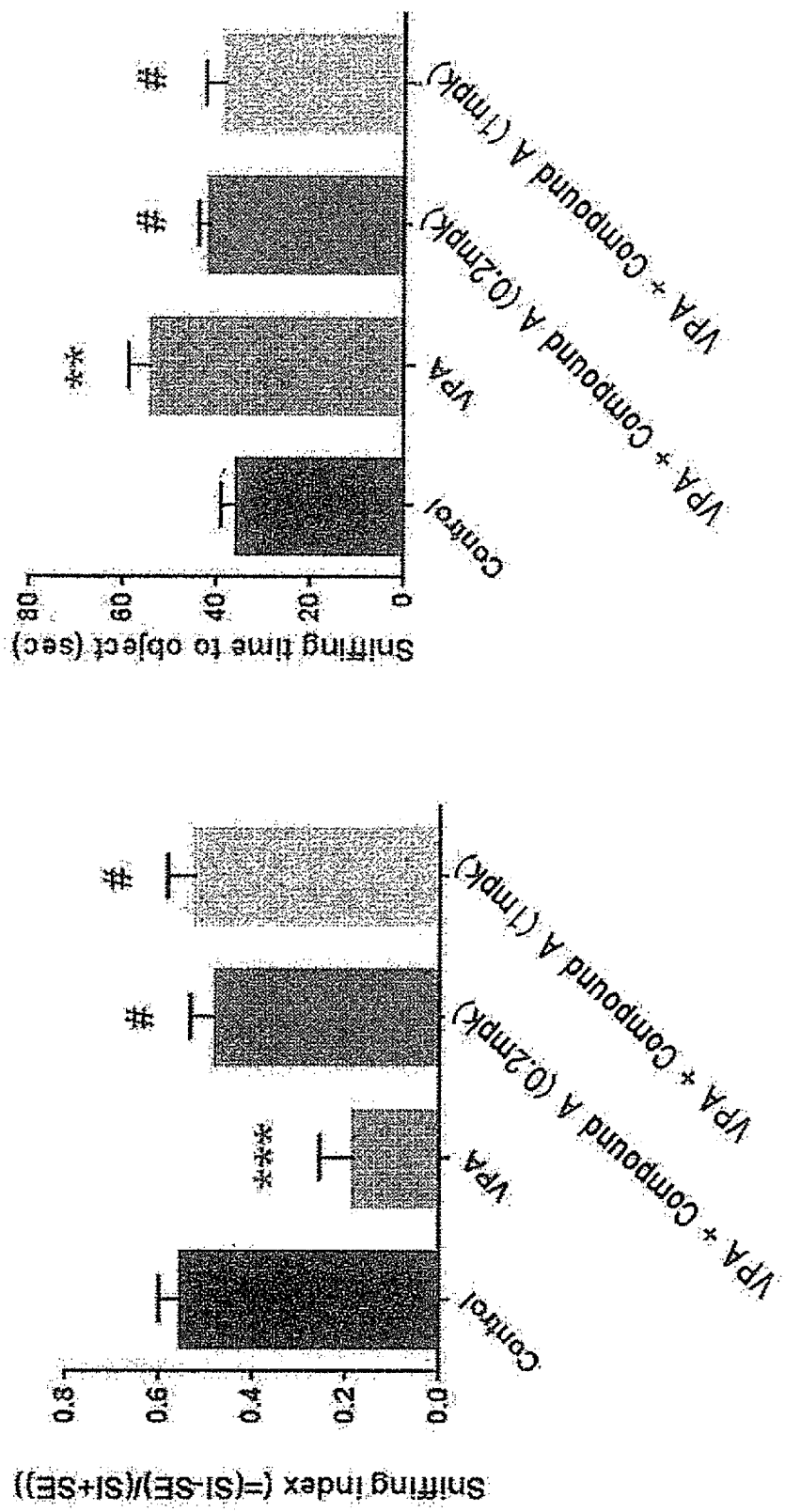

PROPHYLACTIC OR THERAPEUTIC AGENT FOR AUTISM SPECTRUM DISORDER

CROSS-REFERENCE TO RELATED APPLICATION(S)

This is a U.S. national stage entry of International Patent Application No. PCT/JP2017/000166, filed on Jan. 5, 2017, which claims priority to U.S. Provisional Patent Application No. 62/276,354, filed on Jan. 8, 2016, the entire contents of each of which are fully incorporated herein by reference.

TECHNICAL FIELD

The present invention relates to a medicament containing a compound possibly having melatonin receptor affinity and expected to be effective for the prophylaxis or treatment of an autism spectrum disorder.

BACKGROUND OF THE INVENTION

Autistic spectrum disorder is said to be one of neurodevelopmental disorders characterized by the symptoms of social disorder (e.g., social communication disturbance, interpersonal mutual reaction disorder and the like), restricted repetitive modalities (e.g., behavior, interests, activities and the like) and the like (non-patent document 1). At present, a treatment method has not been established yet, and improvement of life has been attempted by prescribing drugs. For example, antipsychotic drugs are used for preventing aggressive behaviors and self-injurious behaviors, which are behavioral disorders associated with autism spectrum disorder. However, it is a symptomatic treatment and does not aim at permanent cure.

Therefore, a therapeutic drug effective for an autism spectrum disorder (particularly, medicament effective for social disorder) has been awaited at the medical site.

Non-patent document 2 discloses that ramelteon was administered to two patients with insomnia accompanied by autism to confirm a therapeutic effect of ramelteon on sleep disorder, and evaluates items relating to sleep disorder.

Patent document 1 discloses a combined use of 5HTR agent and the like and ramelteon, and discloses autism as an application.

Patent document 2 discloses (S)—N-[2-(2-methyl-7,8-dihydro-6H-indeno[5,4-d][1,3]oxazol-8-yl)ethyl]acetamide.

Non-patent document 3 suggests that the amount of melatonin decreases in patients with an autistic spectrum disorder and that ASMT involved in melatonin synthesis in the body is involved.

Non-patent document 4 discloses the results that melatonin metabolite (6-SM) in the urine of autism patients decreases during daytime, in the night and throughout the day, the results that the amount of urinary 6-SM at night and the severity of autism such as language ability and the like show a negative correlation, and the results that the amount of urinary 6-SM during the day and the IQ score and the like show a positive correlation.

Non-patent document 5 suggests that melatonin has a therapeutic effect on sleep disorder in children with insomnia and sleep disorder accompanied by autism spectrum disorder and vulnerability X (Fragile X) syndrome.

Non-patent document 6 reports that there are six tests in the past in which improvement of day-to-day behavior by nocturnal administration of melatonin was reported in autistic spectrum disorder patients, and the like.

DOCUMENT LIST

Patent Documents patent document 1: WO 2007/134077
patent document 2: WO 2007/148808

Non-Patent Documents non-patent document 1: Diagnostic and Statistical Manual of Psychiatric disorders, 5th Edition [DSM-5], p. 50-59
non-patent document 2: Stigler K. A., et., J Child Adolesc Psychopharmacol. 2006 October; 16(5):631-6
non-patent document 3: Melke J et. al., Abnormal melatonin synthesis in autism spectrum disorders., Mol Psychiatry. 2008 January; 13(1):90-8
non-patent document 4: Tordjman S et. al., Day and nighttime excretion of 6-sulphatoxymelatonin in adolescents and young adults with autistic disorder., Psychoneuroendocrinology. 2012 December; 37(12):1990-7
non-patent document 5: Wirojanan J et. al., The efficacy of melatonin for sleep problems in children with autism, fragile X syndrome, or autism and fragile X syndrome., J Clin Sleep Med. 2009 Apr. 15; 5(2):145-50
non-patent document 6: Rossignol D A et. al., Melatonin in autism spectrum disorders: a systematic review and meta-analysis. Dev Med Child Neurol., 2011 Sepember; 53(9): 783-92

SUMMARY OF THE INVENTION

Problems to be Solved by the Invention

An object of the present invention is to provide a medicament containing a compound possibly having melatonin receptor affinity and expected to be effective for the prophylaxis or treatment of an autism spectrum disorder.

Means of Solving the Problems

The present inventors have conducted intensive studies and found that the below-mentioned compound of the present invention may be effective for the prophylaxis or treatment of an autism spectrum disorder, which resulted in the completion of the present invention.

That is, the present invention relates to

[1] a prophylactic or therapeutic agent for an autism spectrum disorder comprising a compound selected from
N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide, N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof (sometimes to be abbreviated as "the compound of the present invention" in the present specification) as an active ingredient (sometimes to be abbreviated as "the agent of the present invention" in the present specification);

[2] a prophylactic or therapeutic agent for an autism spectrum disorder comprising (S)—N-[2-(2-methyl-7,8-dihydro-6H-indeno[5,4-d][1,3]oxazol-8-yl)ethyl]acetamide or a salt thereof as an active ingredient;

[3] a method for preventing or treating an autism spectrum disorder comprising administering an effective amount of a compound selected from
(N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof to a mammal;

[4] a method for preventing or treating an autism spectrum disorder comprising administering an effective amount of (S)—N-[2-(2-methyl-7,8-dihydro-6H-indeno[5,4-d][1,3]oxazol-8-yl)ethyl]acetamide or a salt thereof to a mammal;

[5] a compound selected from
N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof for use as a prophylactic or therapeutic agent for an autism spectrum disorder;

[6] (S)—N-[2-(2-methyl-7,8-dihydro-6H-indeno[5,4-d][1,3]oxazol-8-yl)ethyl]acetamide or a salt thereof for use in the prophylaxis or treatment of an autism spectrum disorder;

[7] use of a compound selected from
(N-[2-(2-methyl-6,7-dihydro-8H-indeno[5,4-d][1,3]oxazol-8-ylidene)ethyl]acetamide, N-[2-(2-methyl-6H-indeno[5,4-d][1,3]oxazol-8-yl)ethyl]ac-
etamide,
N-[2-(2-methyl-6,7-dihydro-8H-indeno[5,4-d][1,3]oxazol-
8-ylidene)ethyl]propionamide,
N-{2-[2-(4-phenylbutyl)-6,7-dihydro-8H-indeno[5,4-d][1,
3]oxazol-8-ylidene]ethyl}acetamide,
N-[2-(2-methyl-6,7-dihydro-8H-indeno[5,4-d][1,3]thiazol-
8-ylidene)ethyl]acetamide,
N-[2-(2-methyl-7,8-dihydro-6H-indeno[5,4-d][1,3]oxazol-
8-yl)ethyl]acetamide,
(R)—N-[2-(2-methyl-7,8-dihydro-6H-indeno[5,4-d][1,3]
oxazol-8-yl)ethyl]acetamide,
(S)—N-[2-(2-methyl-7,8-dihydro-6H-indeno[5,4-d][1,3]
oxazol-8-yl)ethyl]acetamide,
N-[2-(2-methyl-7,8-dihydro-6H-indeno[5,4-d][1,3]oxazol-
8-yl)ethyl]propionamide,
(R)—N-[2-(2-methyl-7,8-dihydro-6H-indeno[5,4-d][1,3]
oxazol-8-yl)ethyl]propionamide,
(S)—N-[2-(2-methyl-7,8-dihydro-6H-indeno[5,4-d][1,3]
oxazol-8-yl)ethyl]propionamide,
N-[2-(2-methyl-7,8-dihydro-6H-indeno[5,4-d][1,3]thiazol-
8-yl) ethyl]acetamide,
(R)—N-[2-(2-methyl-7,8-dihydro-6H-indeno[5,4-d][1,3]
thiazol-8-yl)ethyl]acetamide,
(S)—N-[2-(2-methyl-7,8-dihydro-6H-indeno[5,4-d][1,3]
thiazol-8-yl)ethyl]acetamide,
N-[2-(2-ethyl-7,8-dihydro-6H-indeno[5,4-d][1,3]oxazol-8-
yl)ethyl]acetamide,
(R)—N-[2-(2-ethyl-7,8-dihydro-6H-indeno[5,4-d][1,3]ox-
azol-8-yl)ethyl]acetamide,
(S)—N-[2-(2-ethyl-7,8-dihydro-6H-indeno[5,4-d][1,3]ox-
azol-8-yl)ethyl]acetamide,
N-[2-(2-methoxy-7,8-dihydro-6H-indeno[5,4-d][1,3]ox-
azol-8-yl)ethyl]acetamide,
(R)—N-[2-(2-methoxy-7,8-dihydro-6H-indeno[5,4-d][1,3]
oxazol-8-yl)ethyl]acetamide, and
(S)—N-[2-(2-methoxy-7,8-dihydro-6H-indeno[5,4-d][1,3]
oxazol-8-yl)ethyl]acetamide
or a salt thereof in the production of a prophylactic or therapeutic drug for an autism spectrum disorder;
[8] use of (S)—N-[2-(2-methyl-7,8-dihydro-6H-indeno[5,4-d][1,3]oxazol-8-yl)ethyl]acetamide or a salt thereof in the production of a prophylactic or therapeutic drug for an autism spectrum disorder;
and the like.

Effect of the Invention

According to the present invention, a medicament containing a compound possibly having melatonin receptor affinity as an active ingredient and expected to be effective for the prophylaxis or treatment of an autism spectrum disorder can be provided.

BRIEF DESCRIPTION OF THE DRAWINGS

FIG. 1 is a graph showing the effect of the compound of the present invention on the social disorders of rat valproic acid-exposed autism model (Sniffing index and Sniffing time to cylinder with object (inanimate object) (Sniffing time to object)).

DETAILED DESCRIPTION OF THE INVENTION

Of the compounds of the present invention, (S)—N-[2-(2-methyl-7,8-dihydro-6H-indeno[5,4-d][1,3]oxazol-8-yl) ethyl]acetamide is preferable.

As the salt of the compound of the present invention, a pharmacologically acceptable salt and the like are used. Examples thereof include salts with inorganic bases, salts with organic bases, salts with inorganic acids, salts with organic acids, salts with basic or acidic amino acids and the like. Preferable examples of the salts with inorganic bases include alkali metal salts such as sodium salt, potassium salt and the like, alkaline earth metal salts such as calcium salt, magnesium salt and the like, aluminum salt, ammonium salt and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like and preferable examples of the salts with acidic amino acids include salts with aspartic acid, glutamic acid and the like.

Particularly, a pharmaceutically acceptable salt is preferable. Examples thereof when the compound of the present invention has a basic functional group include salts with inorganic acids such as hydrochloric acid, hydrobromic acid, nitric acid, sulfuric acid, phosphoric acid and the like, and salts with organic acids such as acetic acid, phthalic acid, fumaric acid, tartaric acid, maleic acid, citric acid, succinic acid, methanesulfonic acid, p-toluenesulfonic acid and the like. Examples thereof when the compound of the present invention has an acidic functional group include alkali metal salts such as sodium salt, potassium salt and the like, alkaline earth metal salts such as calcium salt, magnesium salt and the like, ammonium salt and the like.

The compound of the present invention may be a hydrate or a non-hydrate.

The compound of the present invention can be produced according to a method known per se, for example, the production method described in WO 2007/148808 filed on Jun. 18, 2007 as a PCT application and published or a method analogous thereto.

The compound of the present invention may be a crystal, and both a single crystal and crystal mixtures are encompassed in the compound of the present invention. The crystal can be produced by crystallization by applying a crystallization method known per se.

The compound of the present invention or a salt thereof may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

The compound of the present invention encompasses solvates (e.g., hydrate) and non-solvates within the scope thereof. The compound of the present invention may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope may be used, for example, as a tracer used for Positron Emission Tomography (PET) (PET tracer), and may be useful in the field of medical diagnosis and the like.

When the compound of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in the compound of the present invention.

In the compound of the present invention, stereoisomers may be generated depending on the kind of the substituent. Such isomers singly or a mixture thereof are also encompassed in the present invention.

The compound of the present invention may be used as a prodrug. The prodrug of the compound of the present invention means a compound which can be converted into the compound of the present invention by reaction with an enzyme, gastric acid, or the like under physiological conditions in the living body. In other words, it means a compound which can be converted into the compound of the present invention by enzymatic oxidation, reduction, hydrolysis or the like, or a compound which can be converted into the compound of the present invention by hydrolysis with gastric acid or the like.

The compound of the present invention may be useful as a prophylactic or therapeutic agent for an autism spectrum disorder [e.g., autism spectrum disorders with social disability (e.g., social communication impairments, interpersonal mutual reaction disorder etc.), autism spectrum disorders with restricted repetitive patterns (e.g., behavior, interests, activities etc.), pervasive developmental disorders, autism (e.g., childhood autism, infantile autism, high functioning autism, childhood psychosis, Kanner syndrome, atypical autism, etc.), Rett syndrome, Asperger syndrome (e.g., autistic psychopathy, schizophrenia disorder, etc.), childhood disintegrative disorder (e.g., infantile dementia, disintegrative psychosis, Heller's syndrome, symbiotic psychosis, etc.), Down's syndrome, Kabuki syndrome, fragile Syndrome X syndrome, Kleefstra syndrome, Rubinstein-Taybi syndrome, neurofibromatosis type 1 (NF1), Noonan syndrome, tuberous sclerosis, Coffin-Lowry syndrome, Sotos syndrome, Smith-Magenis syndrome, Weaver's syndrome, Cornelia de Lange syndrome, Beckwith-Wiedemann syndrome, Angelman's syndrome, 5p syndrome, 4p syndrome, 18 trisomy syndrome, 13 trisomy syndrome, chromosomal abnormality syndrome, CFC syndrome, Marfan syndrome, Costello syndrome, CHARGE syndrome, Werdnig-Hoffman disease, Dubowitz disease, Kugelberg-Welander disease, intellectual disability group (e.g., intellectual disability, global developmental delay, wisdom delay, intelligence low rank, mental retardation, stupidity, foolishness, idiocy, intelligence defect etc.), communication disorders (e.g., language disorder, speech sound disorder, childhood-onset fluency disorder, social communication disorder etc.), specific learning disorder, motor disorders (e.g., developmental coordination disorder, stereotypic movement disorder etc.), tic disorder group (e.g., Tourette's disorder, persistent motor or vocal tic disorder, provisional tic disorder etc.), learning disorder (e.g., dyslexia, dyscalculia, dysgraphia etc.), selective mutism, boundary intelligence, autism spectrum disorder with intellectual disorder, autism spectrum disorder with language disorder, autism spectrum disorder with tension, other neurodevelopment, autism spectrum disorder with mental disease or behavior disorder (e.g., attention deficit/hyperactivity disorder, coordination disorder, destructive behavior, impulse control disorder, behavior disorder, anxiety, depression, bipolar disorder, tic disorder, Tourette disorder, aggressive behavior, self-injury behavior, eating disorder, excretory disorders, sleeping disorders, etc.), autism spectrum disorder with epilepsy] in mammals (e.g., mouse, rat, hamster, rabbit, cat, dog, bovine, sheep, monkey, human and the like).

The compound of the present invention may have high affinity for melatonin receptors (MT1 receptor, MT2 receptor). The compound of the present invention may act as a melatonin agonist and may be useful as a composition having melatonin receptor affinity, particularly, a melatonin receptor agonist.

Therefore, superior treatment effects for the above-mentioned diseases can be expected.

The compounds having melatonin receptor affinity and described in the specifications as filed of WO 96/08466 filed on Sep. 11, 1995 and published, WO 97/01539 filed on Jun. 26, 1996 and published, WO 97/05098 filed on Jul. 25, 1996 and published, WO 97/32871 filed on Mar. 5, 1997 and published, WO 2008/069311 filed on Dec. 7, 2007 and published, WO 2008/084717 filed on Dec. 27, 2007 and published, and WO 2008/136382 filed on Apr. 25, 2008 and published may also be useful for the prophylaxis, improvement of the symptoms, suppression of progression or treatment of the diseases described above, specifically, an autism spectrum disorder and the like.

Furthermore, a compound represented by the formula

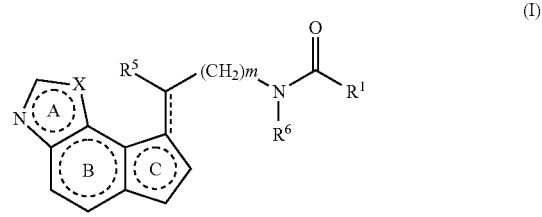

(I)

wherein
R$^1$ is a hydrocarbon group optionally having substituent(s), amino optionally having substituent(s), hydroxy optionally having substituent(s) or a heterocyclic group optionally having substituent(s);
R$^5$ is a hydrogen atom, a halogen atom, a hydrocarbon group optionally having substituent(s), amino optionally having substituent(s), hydroxy optionally having substituent(s) or mercapto optionally having substituent(s);
R$^6$ is a hydrogen atom or a hydrocarbon group optionally having substituent(s);
X is an oxygen atom or a sulfur atom;
m is 0, 1 or 2;
ring A is a 5-membered ring optionally having substituent(s);
ring B is a 6-membered ring optionally having substituent(s);
ring C is a 5-membered ring optionally having substituent(s); and ⁝⁝⁝⁝
is a single bond or a double bond, or a salt thereof (sometimes to be abbreviated as "compound (I)" in the present specification), which is described in WO 2007/148808, may also be useful for the prophylaxis or treatment of an autism spectrum disorder.

Of compounds (I), a compound represented by the formula

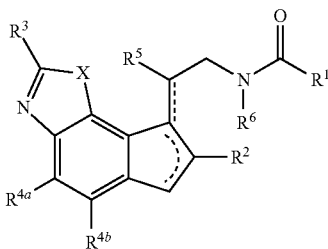

(I')

wherein

R$^1$ is C$_{1-6}$ alkyl optionally having substituent(s), C$_{3-6}$ cycloalkyl optionally having substituent(s) or C$_{2-6}$ alkenyl optionally having substituent(s);

R$^2$ is a hydrogen atom, a hydrocarbon group optionally having substituent(s) or a heterocyclic group optionally having substituent(s);

R$^3$ is a hydrogen atom, C$_{1-6}$ alkyl optionally having substituent(s), C$_{2-6}$ alkenyl optionally having substituent(s) or amino optionally having substituent(s);

R$^{4a}$ and R$^{4b}$ are the same or different and each is a hydrogen atom, a halogen atom, hydroxy optionally having substituent(s) or C$_{1-6}$ alkyl optionally having substituent(s);

R$^5$ is a hydrogen atom or C$_{1-6}$ alkyl optionally having substituent(s); and R$^6$ is a hydrogen atom or C$_{1-6}$ alkyl optionally having substituent(s), or a salt thereof is preferable.

In the aforementioned formula, the ring represented by

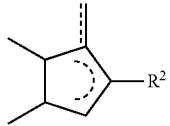

is

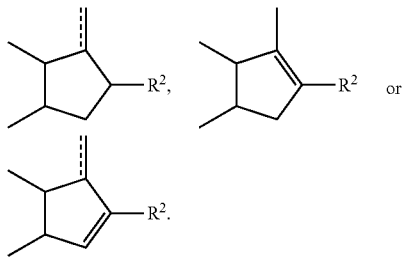

Of compounds (I), particularly a compound represented by the formula

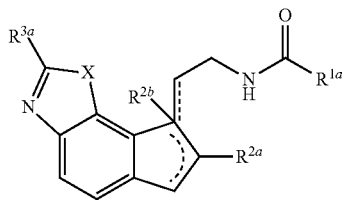

wherein

R$^{1a}$ is (a) C$_{1-6}$ alkyl optionally having 1 to 3 substituents selected from C$_{1-6}$ alkyl-carbonyloxy, hydroxy and halogen atom, (b) C$_{3-6}$ cycloalkyl, (c) phenyl or (d) mono- or di-C$_{1-6}$ alkylamino;

R$^{2a}$ is a hydrogen atom or C$_{1-6}$ alkyl;

R$^{2b}$ is a hydrogen atom or hydroxy; and

R$^{3a}$ is (a) a hydrogen atom, (b) C$_{1-6}$ alkyl optionally having 1 to 3 substituents selected from phenyl, hydroxy, a halogen atom, C$_{1-6}$ alkyl-carbonyl, C$_{7-13}$ aralkyloxy and pyridyl, (c) C$_{3-6}$ cycloalkyl, (d) phenyl, (e) C$_{1-6}$ alkoxy, (f) mercapto, (g) C$_{1-6}$ alkylthio or (h) mono- or di-C$_{1-6}$ alkylamino, or a salt thereof is preferable.

In the aforementioned formula, the ring represented by

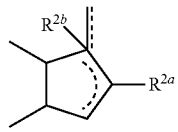

is

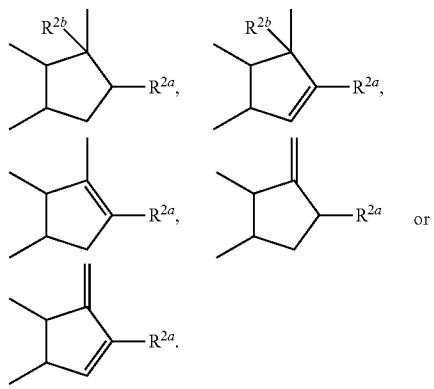

In addition, medicaments such as tasimelteon, agomelatine, melatonin sustained release preparation, melatonin sustained release preparation for children and the like may also be useful for the prophylaxis or treatment of an autism spectrum disorder.

The compound of the present invention may have superior properties as a pharmaceutical product since it can be expected to be superior in solubility in water, the Japanese Pharmacopoeia dissolution test 2nd fluid or the Japanese Pharmacopoeia disintegration test 2nd fluid, can be expected to be superior in pharmacokinetics (e.g., drug half-life in blood, intracerebral transferability, metabolic stability, CYP inhibition), can be expected to have low toxicity (e.g., more superior as medicament in terms of acute toxicity, chronic toxicity, genetic toxicity, reproductive toxicity, cardiotoxicity, drug interaction, carcinogenicity, phototoxicity and the like), can be expected to show few side effects and the like. Therefore, the compound of the present invention can be safely administered orally or parenterally to mammals (e.g., mouse, rat, hamster, rabbit, cat, dog, bovine, sheep, monkey, human and the like). The "parenteral" includes intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion.

The agent of the present invention may take any form of a solid preparation such as powder, granule, tablet, capsule, orally disintegrable film or the like, or liquid such as syrup, emulsion, injection or the like.

The agent of the present invention can be produced by a conventionally-used method, for example, blending, kneading, granulation, tableting, coating, sterilization treatment, emulsification or the like according to the form thereof. As for the production of the preparation, for example, each section of the Japanese Pharmacopoeia preparation General Rules and the like can be referred to. The agent of the present invention may also be formulated as a sustained-release preparation containing the active ingredient and a biodegradable polymer compound. Such sustained-release preparation can be formulated according to the method described in JP-A-9-263545.

In the agent of the present invention, the content of the compound of the present invention varies depending on the form of the preparation. It is generally about 0.01-100 wt %, preferably about 0.1-50 wt %, further preferably about 0.5-20 wt %, as the amount of the compound of the present invention or a salt thereof relative to the whole preparation (whole medicament).

The compound of the present invention may be administered orally or parenterally as it is or in the form of a solid agent such as powder, fine granule, granule, tablet, capsule or the like or a liquid agent such as injection or the like by mixing with an appropriate pharmacologically acceptable carrier, for example, excipient (e.g., starch, lactose, sucrose, calcium carbonate, calcium phosphate and the like), binder (e.g., starch, gum arabic, carboxymethylcellulose, hydroxypropylcellulose, crystalline cellulose, alginic acid, gelatin, polyvinylpyrrolidone and the like), lubricant (e.g., stearic acid, magnesium stearate, calcium stearate, talc and the like), disintegrant (e.g., calcium carboxymethylcellulose, talc and the like), diluent (e.g., water for injection, saline and the like), additive (e.g., stabilizer, preservative, colorant, flavor, solubilizing agent, emulsifier, buffering agent, isotonic agent and the like) as necessary and the like by a conventional method. When the compound of the present invention or a salt thereof is formulated as a preparation for topical administration, it can be directly administered to the affected parts of an articular disease and the like. In this case, it is preferable to form an injection. The compound can be administered as a parenteral agent for topical administration (e.g., intramuscular injection, subcutaneous injection, organ injection, injection into joint part and the like, a solid preparation such as implant, granule, powder and the like, liquid such as suspension and the like, ointment etc.) or the like.

For example, when an injection is formed, the compound of the present invention is formulated into an aqueous suspension together with dispersing agent (e.g., surfactant such as Tween 80, HCO-60 and the like, polysaccharide such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffering agent (e.g., calcium carbonate etc.), pH adjuster (e.g., sodium phosphate, potassium phosphate etc.) and the like, whereby a practical preparation for injection can be obtained. Alternatively, the compound is dispersed together with a vegetable oil such as sesame oil, corn oil etc., or a mixture thereof with phospholipid such as lecithin and the like or medium-chain fatty acid triglyceride (e.g., miglyol 812 etc.) to obtain an oily suspension to give an injection that can be used in practice.

The dose of the compound of the present invention varies depending on the subject of administration, administration route, target disease, symptom and the like. For example, for oral administration to an adult, the single dose is generally about 0.01-100 mg/kg body weight, preferably 0.1-50 mg/kg body weight, further preferably 0.5-mg/kg body weight. This amount may be administered in one to three portions per day.

The agent of the present invention may be used solely or in the form of a pharmaceutical composition obtained by mixing with a pharmacologically acceptable carrier according to a method known per se (e.g., the method described in the Japanese Pharmacopoeia etc.) as the production method of a pharmaceutical preparation. The agent of the present invention may be safely administered as a pharmaceutical composition, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop or the like, orally or parenterally (e.g., intravenous, intramuscular, subcutaneous, intraorgan, intranasal, intradermal, instillation, intracerebral, intrarectal, intravaginal and intraperitoneal administrations, and administration to lesion and the like).

As the aforementioned "pharmacologically acceptable carrier", various organic or inorganic carriers conventionally used as preparation materials (starting materials) may be used. For example, excipient, lubricant, binder and disintegrant and the like may be used for solid preparations, and solvent, solubilizing agent, suspending agent, isotonic agent, buffering agent, and soothing agent and the like may be used for liquid preparations. Where necessary, preparation additives such as preservative, antioxidant, colorant, sweetening agent and the like may be used.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like;

hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

The pharmaceutical composition can be produced according to a conventional method by adding the compound of the present invention in a proportion of generally 0.01-100% (w/w), preferably 0.1-95% (w/w), relative to the total amount of the preparation, though subject to change depending on the dosage form, administration method, carrier and the like.

The compound of the present invention can be expected to have extremely low toxicity, can be used for the prophylaxis or 35 treatment of an autism spectrum disorder by combining with other medicament, and can be expected to show a superior prophylactic or therapeutic effect by such combined use with said other medicament. It can also be expected to reduce side effects of other prophylactic or therapeutic agents for an autism spectrum disorder by reducing the dose thereof by such combination therapy.

As such medicaments that can be used in combination with the compound of the present invention (hereinafter to be abbreviated as concomitant drug), for example, "other prophylactic or therapeutic agents for an autism spectrum disorder" (e.g., serotonin.dopamine antagonist (risperidone, olanzapine, quetiapine, clozapine, ziprasidone and the like), dopamine partial agonist (aripiprazole and the like) and the like) can be mentioned.

In the following, combined use of the compound of the present invention and a concomitant drug is indicated by "the combination agent of the present invention".

Two or more kinds of the above-mentioned concomitant drugs may be used in combination at an appropriately ratio.

When the compound of the present invention is used in combination with concomitant drugs, the amounts of the drugs may be decreased within a safe range in consideration of the counter effect of the drugs. Therefore, the counter effect presumably induced by these drugs can be prevented safely.

The compound of the present invention may be used in combination with a non-drug therapy. Specific examples of the non-drug therapy include (1) surgery; (2) pressurized chemotherapy using angiotensin II and the like; (3) gene therapy; (4) hyperthermia therapy; (5) cryotherapy; (6) laser ablation method; (7) radiation therapy; (8) immunotherapy; (9) regenerative therapy; (10) cell therapy method; (11) psychotherapy or psychosocial therapy.

These concomitant drugs may be free forms or pharmaceutically acceptable salts. Examples of such salt when the drug has an acidic functional group include inorganic salts such as alkali metal salt (e.g., sodium salt, potassium salt and the like), alkaline earth metal salt (e.g., calcium salt, magnesium salt, barium salt and the like) and the like, ammonium salt and the like. Examples thereof when the drug has a basic functional group include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like. The concomitant drugs exemplified here can be easily obtained as commercially available products or can be produced according to a known method.

When the compound of the present invention and a concomitant drug are used in combination, examples of the administration mode include the following:

(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention; the concomitant drug, or in the reverse order) and the like.

From the aspect of convenience of the patients, administration of a single preparation obtained by simultaneously processing the compound of the present invention and the concomitant drug is a particularly preferable embodiment.

The dose of the concomitant drug may be appropriately selected using the clinically-used dose as the standard. In addition, the mixing ratio of the compound of the present invention and the concomitant drugs may be appropriately selected according to the subject of administration, administration route, symptom, the kind of the concomitant drug used and the like. Generally, it may be determined using the general dose of the concomitant drug used as the standard. When the subject of administration is human, for example, 0.01-100 parts by weight of the concomitant drug is used per part by weight of the compound of the present invention.

The combination agent in the present invention may be used as a pharmaceutical composition, like the agent of the present invention, which is obtained by mixing the compound of the present invention or(and) the above-mentioned concomitant drug are mixed with a pharmacologically acceptable carrier.

The mixing ratio of the compound of the present invention and a concomitant drug in the combination agent of the present invention may be appropriately selected based on the subject of administration, administration route, target disease, symptom, combination and the like.

For example, while the content of the compound of the present invention in the combination agent of the present invention varies depending on the preparation form, it is generally about 0.01 to about 100 wt %, preferably about 0.1 to about 50 wt %, more preferably about 0.5 to about wt %, of the whole preparation.

The content of the concomitant drug in the combination agent of the present invention varies depending on the preparation form, and generally about 0.01 to about 100 wt %, preferably about 0.1 to about 50 wt %, further preferably about 0.5 to about wt %, of the whole preparation.

While the content of the additive such as a carrier and the like in the combination agent of the present invention varies depending on the form of a preparation, it is generally about 1 to about 99.99 wt %, preferably about 10 to about 90 wt %, based on the whole preparation.

When the compound of the present invention and the concomitant drug are separately prepared, the contents thereof are the same as above.

EXAMPLES

While the present invention is explained in detail by further referring to the following Production Examples, Examples and Preparation Example, they are mere Production Examples, Examples and Preparation Example and do not limit the present invention.

The compounds in the following Production Examples can be produced by a method known per se, for example, Reference Examples and Examples described in WO 2007/148808 filed on Jun. 18, 2007 as a PCT application and published or a method analogous thereto.

In the following Examples and Preparation Example, (S)—N-[2-(2-methyl-7,8-dihydro-6H-indeno[5,4-d][1,3]oxazol-8-yl)ethyl]acetamide (compound of Production Example 12) is compound A.

Production Example 1

N-[2-(6,7-dihydro-8H-indeno[5,4-d][1,3]oxazol-8-ylidene)ethyl]acetamide

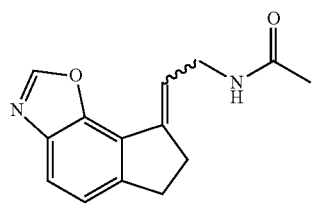 [SMILES: CC(=O)NCC=C1CCc2ccc3ncoc3c21]

Production Example 2

N-[2-(6,7-dihydro-8H-indeno[5,4-d][1,3]oxazol-8-ylidene)ethyl]propionamide

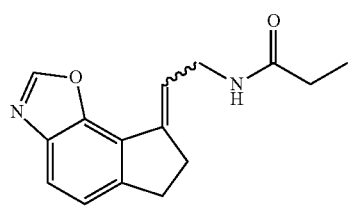 [SMILES: CCC(=O)NCC=C1CCc2ccc3ncoc3c21]

Production Example 3

N-[2-(2-methyl-6,7-dihydro-8H-indeno[5,4-d][1,3]oxazol-8-ylidene)ethyl]acetamide

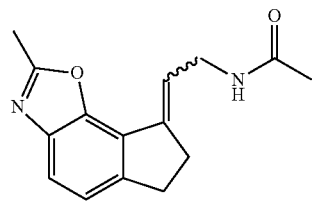 [SMILES: CC(=O)NCC=C1CCc2ccc3nc(C)oc3c21]

Production Example 4

N-[2-(2-methyl-6H-indeno[5,4-d][1,3]oxazol-8-yl)ethyl]acetamide

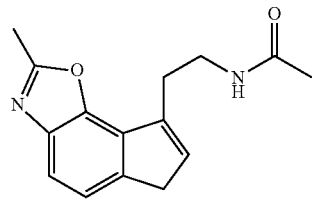 [SMILES: CC(=O)NCCC1=CCc2ccc3nc(C)oc3c21]

Production Example 5

N-[2-(2-methyl-6,7-dihydro-8H-indeno[5,4-d][1,3]oxazol-8-ylidene)ethyl]propionamide

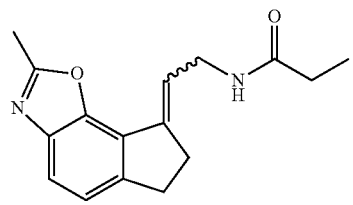 [SMILES: CCC(=O)NCC=C1CCc2ccc3nc(C)oc3c21]

Production Example 6

N-{2-[2-(4-phenylbutyl)-6,7-dihydro-8H-indeno[5,4-d][1,3]oxazol-8-ylidene]ethyl}acetamide

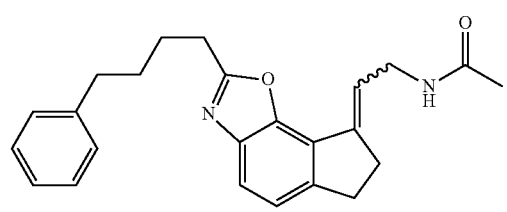 [SMILES: CC(=O)NCC=C1CCc2ccc3nc(CCCCc4ccccc4)oc3c21]

Production Example 7

N-{2-[2-(4-phenylbutyl)-6,7-dihydro-8H-indeno[5,4-d][1,3]oxazol-8-ylidene]ethyl}propionamide

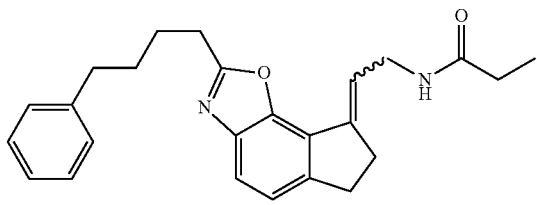 [SMILES: CCC(=O)NCC=C1CCc2ccc3nc(CCCCc4ccccc4)oc3c21]

Production Example 8

N-[2-(2-methyl-6,7-dihydro-8H-indeno[5,4-d][1,3]thiazol-8-ylidene)ethyl]acetamide

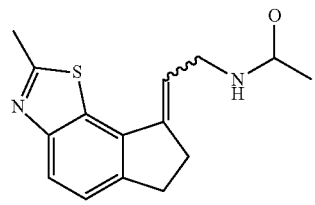

Production Example 9

N-[2-(7,8-dihydro-6H-indeno[5,4-d][1,3]oxazol-8-yl)ethyl]acetamide

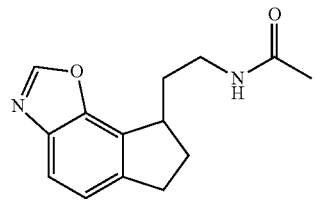 [SMILES: CC(=O)NCCC1CCc2ccc3ncoc3c21]

Production Example 10

N-[2-(7,8-dihydro-6H-indeno[5,4-d][1,3]oxazol-8-yl)ethyl]propionamide

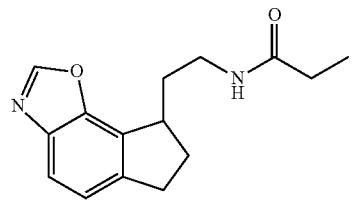 [SMILES: CCC(=O)NCCC1CCc2ccc3ncoc3c21]

Production Example 11

N-[2-(2-methyl-7,8-dihydro-6H-indeno[5,4-d][1,3]oxazol-8-yl)ethyl]acetamide

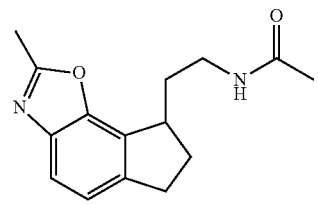 [SMILES: CC(=O)NCCC1CCc2ccc3nc(C)oc3c21]

Production Example 12

(S)—N-[2-(2-methyl-7,8-dihydro-6H-indeno[5,4-d][1,3]oxazol-8-yl)ethyl]acetamide

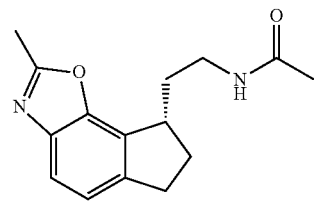 [SMILES: CC(=O)NCC[C@@H]1CCc2ccc3nc(C)oc3c21]

Production Example 13

(R)—N-[2-(2-methyl-7,8-dihydro-6H-indeno[5,4-d][1,3]oxazol-8-yl)ethyl]acetamide

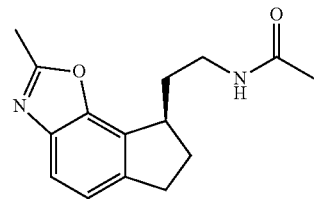 [SMILES: CC(=O)NCC[C@H]1CCc2ccc3nc(C)oc3c21]

Production Example 14

N-[2-(2-methyl-7,8-dihydro-6H-indeno[5,4-d][1,3]oxazol-8-yl)ethyl]propionamide

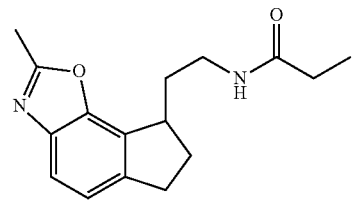 [SMILES: CCC(=O)NCCC1CCc2ccc3nc(C)oc3c21]

Production Example 15

(S)—N-[2-(2-methyl-7,8-dihydro-6H-indeno[5,4-d][1,3]oxazol-8-yl)ethyl]propionamide

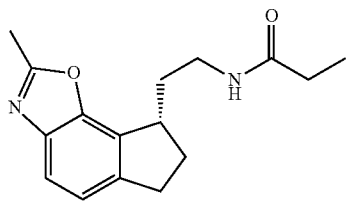

Production Example 16

(R)—N-[2-(2-methyl-7,8-dihydro-6H-indeno[5,4-d][1,3]oxazol-8-yl)ethyl]propionamide

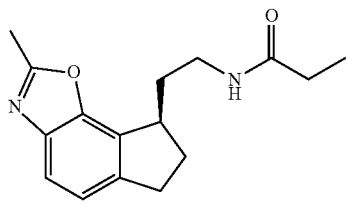 [SMILES: CCC(=O)NCC[C@H]1CCc2ccc3nc(C)oc3c21]

Production Example 17

N-{2-[2-(4-phenylbutyl)-7,8-dihydro-6H-indeno[5,4-d][1,3]oxazol-8-yl]ethyl}acetamide

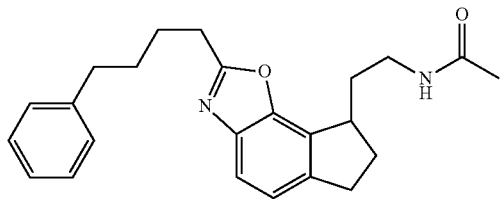 [SMILES: CC(=O)NCCC1CCc2ccc3nc(CCCCc4ccccc4)oc3c21]

Production Example 18

N-{2-[2-(4-phenylbutyl)-7,8-dihydro-6H-indeno[5,4-d][1,3]oxazol-8-yl]ethyl}propionamide

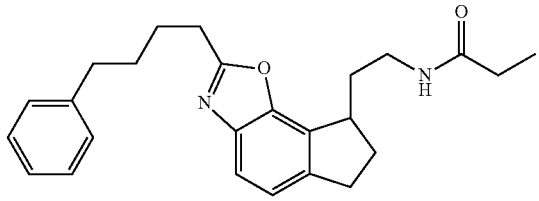 [SMILES: CCC(=O)NCCC1CCc2ccc3nc(CCCCc4ccccc4)oc3c21]

Production Example 19

N-[2-(2-methyl-7,8-dihydro-6H-indeno[5,4-d][1,3]thiazol-8-yl)ethyl]acetamide

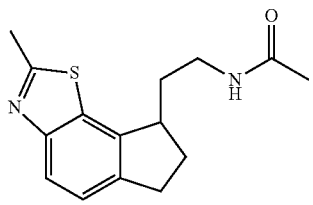 [SMILES: CC(=O)NCCC1CCc2ccc3nc(C)sc3c21]

Production Example 20

(S)—N-[2-(2-methyl-7,8-dihydro-6H-indeno[5,4-d][1,3]thiazol-8-yl)ethyl]acetamide

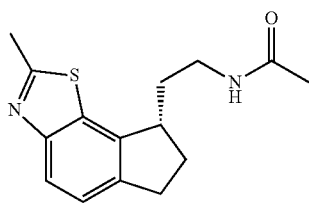

Production Example 21

(R)—N-[2-(2-methyl-7,8-dihydro-6H-indeno[5,4-d][1,3]thiazol-8-yl)ethyl]acetamide

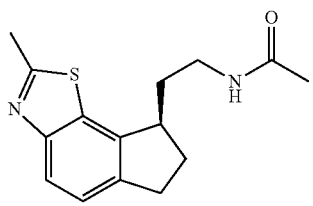 [SMILES: CC(=O)NCC[C@H]1CCc2ccc3nc(C)sc3c21]

Production Example 22

N-[2-(2-ethyl-7,8-dihydro-6H-indeno[5,4-d][1,3]oxazol-8-yl)ethyl]acetamide

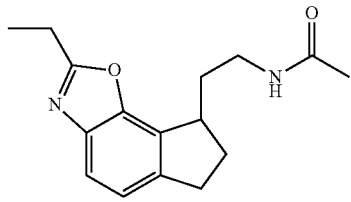 [SMILES: CCc1nc2ccc3c(c2o1)C(CCNC(C)=O)CC3]

Production Example 23

N-{2-[2-(hydroxymethyl)-7,8-dihydro-6H-indeno[5,4-d][1,3]oxazol-8-yl]ethyl}acetamide

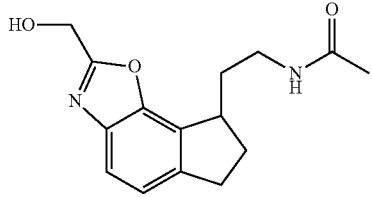 [SMILES: CC(=O)NCCC1CCc2ccc3nc(CO)oc3c21]

Production Example 24

N-[2-(2-isopropyl-7,8-dihydro-6H-indeno[5,4-d][1,3]oxazol-8-yl)ethyl]acetamide

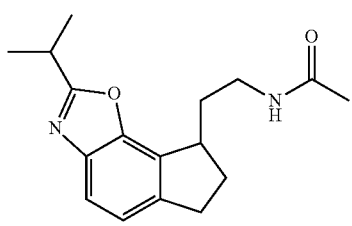 [SMILES: CC(=O)NCCC1CCc2ccc3nc(C(C)C)oc3c21]

Production Example

N-{2-[2-(trifluoromethyl)-7,8-dihydro-6H-indeno[5,4-d][1,3]oxazol-8-yl]ethyl}acetamide

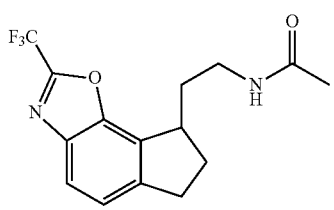 [SMILES: CC(=O)NCCC1CCc2ccc3nc(C(F)(F)F)oc3c21]

Production Example 26

N-{2-[2-(4-hydroxybutyl)-7,8-dihydro-6H-indeno[5,4-d][1,3]oxazol-8-yl]ethyl}acetamide

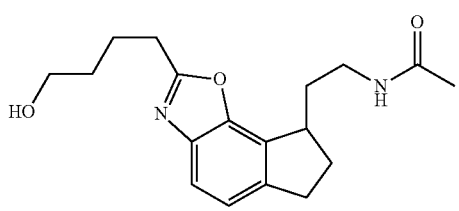 [SMILES: CC(=O)NCCC1CCc2ccc3nc(CCCCO)oc3c21]

Production Example 27

N-{2-[2-(3-hydroxybutyl)-7,8-dihydro-6H-indeno[5,4-d][1,3]oxazol-8-yl]ethyl}acetamide

Production Example 28

N-{2-[2-(3-oxobutyl)-7,8-dihydro-6H-indeno[5,4-d][1,3]oxazol-8-yl]ethyl}acetamide

Production Example 29

N-[2-(2-cyclopropyl-7,8-dihydro-6H-indeno[5,4-d][1,3]oxazol-8-yl)ethyl]acetamide

Production Example 30

N-[2-(2-phenyl-7,8-dihydro-6H-indeno[5,4-d][1,3]oxazol-8-yl)ethyl]acetamide

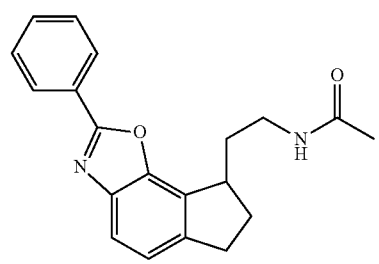 [SMILES: CC(=O)NCCC1CCc2ccc3nc(-c4ccccc4)oc3c21]

Production Example 31

N-[2-(2-benzyl-7,8-dihydro-6H-indeno[5,4-d][1,3]oxazol-8-yl)ethyl]acetamide

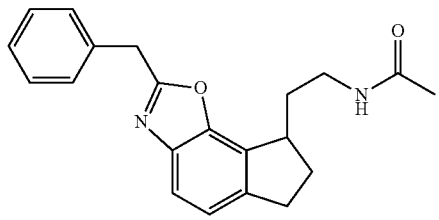 [SMILES: CC(=O)NCCC1CCc2ccc3nc(Cc4ccccc4)oc3c21]

Production Example 32

N-{2-[2-(2-phenylethyl)-7,8-dihydro-6H-indeno[5,4-d][1,3]oxazol-8-yl]ethyl}acetamide

Production Example 33

N-{2-[2-(3-phenylpropyl)-7,8-dihydro-6H-indeno[5,4-d][1,3]oxazol-8-yl]ethyl}acetamide

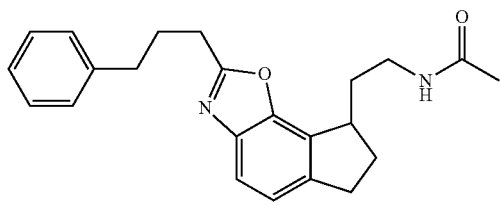

Production Example 34

N-(2-{2-[(benzyloxy)methyl]-7,8-dihydro-6H-indeno[5,4-d][1,3]oxazol-8-yl}ethyl)acetamide

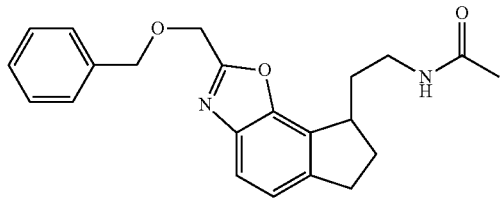 [SMILES: CC(=O)NCCC1CCc2ccc3nc(COCc4ccccc4)oc3c21]

Production Example 35

N-(2-{2-[4-(benzyloxy)butyl]-7,8-dihydro-6H-indeno[5,4-d][1,3]oxazol-8-yl}ethyl)acetamide

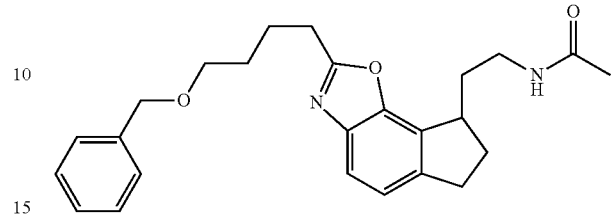

Production Example 36

N-(2-{2-[3-(benzyloxy)butyl]-7,8-dihydro-6H-indeno[5,4-d][1,3]oxazol-8-yl}ethyl)acetamide

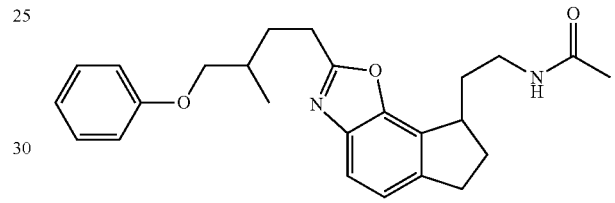

Production Example 37

N-{2-[2-(4-pyridin-2-ylbutyl)-7,8-dihydro-6H-indeno[5,4-d][1,3]oxazol-8-yl]ethyl}acetamide

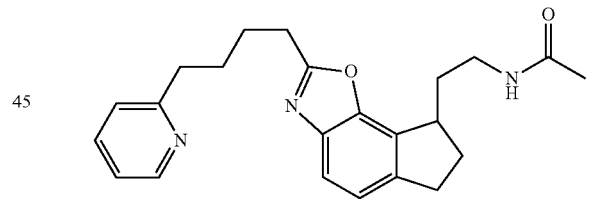

Production Example 38

N-[2-(2-methoxy-7,8-dihydro-6H-indeno[5,4-d][1,3]oxazol-8-yl)ethyl]acetamide

Production Example 39

N-{2-[2-(methylthio)-7,8-dihydro-6H-indeno[5,4-d][1,3]oxazol-8-yl]ethyl}acetamide

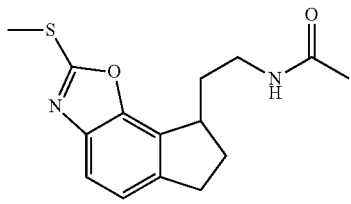 [SMILES: CSc1nc2ccc3c(c2o1)C(CCNC(C)=O)CC3]

Production Example 40

N-{2-[2-(dimethylamino)-7,8-dihydro-6H-indeno[5,4-d][1,3]oxazol-8-yl]ethyl}acetamide

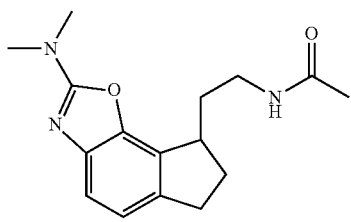 [SMILES: CC(=O)NCCC1CCc2ccc3nc(N(C)C)oc3c21]

Production Example 41

1-methyl-2-{[2-(2-methyl-7,8-dihydro-6H-indeno[5,4-d][1,3]oxazol-8-yl)ethyl]amino}-2-oxoethyl acetate

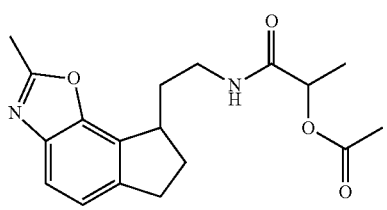 [SMILES: CC(=O)OC(C)C(=O)NCCC1CCc2ccc3nc(C)oc3c21]

Production Example 42

2-hydroxy-N-[2-(2-methyl-7,8-dihydro-6H-indeno[5,4-d][1,3]oxazol-8-yl)ethyl]propanamide

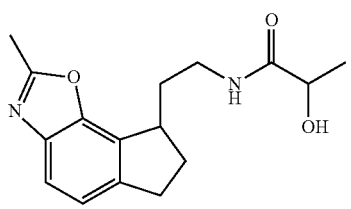 [SMILES: Cc1nc2ccc3c(c2o1)C(CCNC(=O)C(C)O)CC3]

Production Example 43

N-[2-(2-methyl-7,8-dihydro-6H-indeno[5,4-d][1,3]oxazol-8-yl)ethyl]cyclopropanecarboxamide

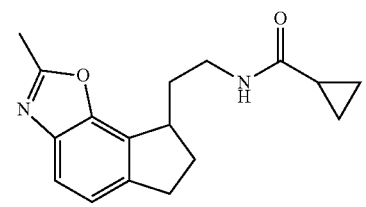 [SMILES: Cc1nc2ccc3c(c2o1)C(CCNC(=O)C1CC1)CC3]

Production Example 44

N-[2-(2-methyl-7,8-dihydro-6H-indeno[5,4-d][1,3]oxazol-8-yl)ethyl]benzamide

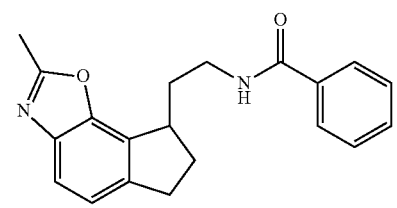 [SMILES: Cc1nc2ccc3c(c2o1)C(CCNC(=O)c1ccccc1)CC3]

Production Example 45

2,2,2-trifluoro-N-[2-(2-methyl-7,8-dihydro-6H-indeno[5,4-d][1,3]oxazol-8-yl)ethyl]acetamide

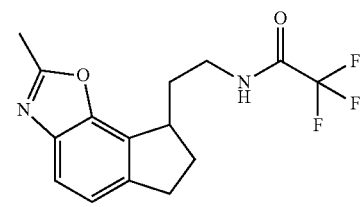 [SMILES: Cc1nc2ccc3c(c2o1)C(CCNC(=O)C(F)(F)F)CC3]

Production Example 46

1-ethyl-3-[2-(2-methyl-7,8-dihydro-6H-indeno[5,4-d][1,3]oxazol-8-yl)ethyl]urea

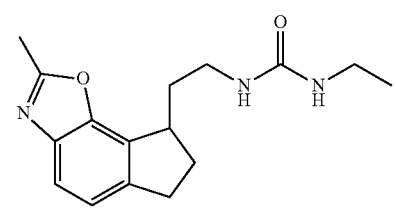 [SMILES: CCNC(=O)NCCC1CCc2ccc3nc(C)oc3c21]

Production Example 47

N-[2-(2-mercapto-7,8-dihydro-6H-indeno[5,4-d][1,3]oxazol-8-yl)ethyl]acetamide

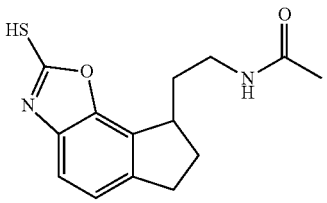 [SMILES: CC(=O)NCCC1CCc2ccc3nc(S)oc3c21]

Production Example 48

N-[2-(8-hydroxy-7-isopropyl-2-methyl-7,8-dihydro-6H-indeno[5,4-d][1,3]oxazol-8-yl)ethyl]acetamide

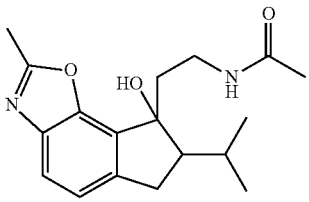 [SMILES: CC(=O)NCCC1(O)c2c(ccc3nc(C)oc23)CC1C(C)C]

Production Example 49

N-[2-(7-isopropyl-2-methyl-6H-indeno[5,4-d][1,3]oxazol-8-yl)ethyl]acetamide

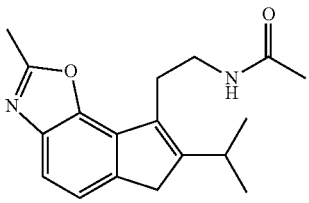 [SMILES: CC(=O)NCCC1=C(C(C)C)Cc2ccc3nc(C)oc3c21]

Example 1

Effect of the compound of the present invention on social disorders in rat valproic acid-exposed autism model Rat embryonic valproic acid-exposed autism model was used for the test. Sodium valproate (VPA) 500 mg/kg (mpk) was intraperitoneally administered to Sprague-Dawley pregnant rats on the 12.5th day in the embryonic stage. The offspring was weaned on the 21st day after birth, and only the male rat was used for the experiment. Compound A (0.2 or 1 mg/kg) was orally administered once a day at 18 o'clock for 14 days from 3 weeks of age after weaning and a behavioral test was conducted at 5 weeks of age. As unknown rat (Stranger rat), a purchased male rat of the same strain and the same week of age was used with no contact with the rat to be tested (test rat) until the day of the test.

In the experiment, a black plastic 3 chamber experimental apparatus (90×60×34 cm, each chamber 30×60×34 cm) was used. The partition of each chamber was made of transparent plastic, with an opening of 10×12 cm at the bottom, through which the rats were allowed to freely move between compartments. One transparent acrylic cylinder (diameter 12 cm, height cm, holes (diameter 1.5 cm) on the side at equal intervals, with black hemispherical metal lid) was installed in the left and right compartments in the experimental apparatus, thereby inhibiting direct contact with the unknown rat.

On the day of the test, the rats to be tested and unknown rats were acclimated to the test environment for 1 hour or more and then the test was started. In the 3 chamber apparatus, a transparent partition plate with no opening was placed to prevent entry into the left and right compartments and the test rats were put in the central compartment for 5 min. After 5 min, the unknown rat was put in one cylinder and an object (white sphere) was put in the other cylinder. The transparent partition plate without opening was gently removed so that the test rats can freely come and go between the left and right compartments. The sniffing to each cylinder (action of sniffing an object or an animal) was visually measured for 10 min. A sniffing index, which is an indicator of interest to other animal, was calculated by the following formula based on the sniffing time to each cylinder for 10 min. The results are shown in FIG. 1.

Sniffing index=((sniffing time (sec) to cylinder with unknown rat)−(sniffing time (sec) to cylinder with object)/((sniffing time (sec) to cylinder with unknown rat))+(sniffing time (sec) to cylinder with object))

In a Sociability test, embryonic valproic acid-exposed rat showed a significant (*p≤0.001) decrease in Sniffing Index, which is an indicator of an interest in other animal and a significant (P≤0.01) increase in sniffing time to cylinder containing object (inanimate object) as compared to the control, based on which a social disorder was acknowledged. In contrast, chronic administration of compound A (0.2 or 1 mg/kg) showed a significant (# P≤0.025) improvement effect on social performance.

Chronic administration of compound A showed effectiveness on the social disorder of the embryonic rat valproic acid-exposed autism model.

Preparation Example 1

Compound A (160 g), lactose (4064 g), and cornstarch (640 g) were uniformly mixed in a fluid bed dryer granulator, and the mixture was granulated while spraying an aqueous solution of hydroxypropylcellulose (160 g) therein and dried therein. The obtained granulated product was crushed using a power mill with a 1.5 mmφ punching screen to give a sieved powder. The sieved powder (3894 g) was measured, cornstarch (124 g) and magnesium stearate (12.4 g) were added thereto, and they were mixed to give granules for tableting. The granules were tableted by a tableting machine with a 7.0 mmφ pounder to a weight of 130 mg to give uncoated tablets. A solution of titanium oxide, yellow ferric oxide dispersed in hydroxypropylmethylcellulose 2910, copolyvidone was sprayed on the obtained uncoated tablets in the film coating machine to give about 25000 film-coated tablets containing 4 mg of compound A per tablet and having the formulation shown in Table 1.

TABLE 1

| composition | amount (mg) |
| --- | --- |
| compound A | 4.0 |
| lactose | 101.6 |
| cornstarch | 20.0 |
| hydroxypropylcellulose | 4.0 |
| magnesium stearate | 0.4 |
| uncoated tablet | 130.0 |
| hydroxypropylmethylcellulose 2910 | 3.74 |
| copolyvidone | 0.75 |
| titanium oxide | 0.5 |
| yellow ferric oxide | 0.01 |
| total | 135.0 |

INDUSTRIAL APPLICABILITY

According to the present invention, a medicament containing a compound possibly having melatonin receptor affinity as an active ingredient and expected to be effective for the prophylaxis or treatment of an autism spectrum disorder can be provided.

This application is based on a Us provisional patent application No. 62/276,354, the contents of which are incorporated in full herein.

The invention claimed is:

1. A method for treating an autism spectrum disorder comprising administering an effective amount of a compound selected from
(N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof to a mammal.

2. A method for treating an autism spectrum disorder comprising administering an effective amount of (S)—N-[2-(2-methyl-7,8-dihydro-6H-indeno[5,4-d][1,3]oxazol-8-yl)ethyl]acetamide or a salt thereof to a mammal.

3. The method of claim 2, further comprising administering an effective amount of other therapeutic agents for autism spectrum disorder.

* * * * *